US008923951B2

(12) United States Patent
Mawhinney et al.

(10) Patent No.: US 8,923,951 B2
(45) Date of Patent: Dec. 30, 2014

(54) DIAGNOSTIC DEVICES USING THERMAL NOISE

(75) Inventors: Daniel D. Mawhinney, Livingston, NJ (US); Fred Sterzer, Princeton, NJ (US)

(73) Assignee: MMTC, Inc., Princeton, NJ (US)

( * ) Notice: Subject to any disclaimer, the term of this patent is extended or adjusted under 35 U.S.C. 154(b) by 585 days.

(21) Appl. No.: 12/985,781

(22) Filed: Jan. 6, 2011

(65) Prior Publication Data

US 2012/0179048 A1 Jul. 12, 2012

(51) Int. Cl.
*A61B 6/00* (2006.01)
*A61B 5/05* (2006.01)

(52) U.S. Cl.
CPC ............... *A61B 6/502* (2013.01); *A61B 6/4417* (2013.01); *A61B 5/0507* (2013.01)
USPC .......................................... 600/427; 600/430

(58) Field of Classification Search
USPC .......... 600/472, 474, 475, 476, 477; 324/637, 324/638, 647; 604/101, 156, 96, 102; 607/101, 156, 96, 102
See application file for complete search history.

(56) References Cited

U.S. PATENT DOCUMENTS

| | | | | |
|---|---|---|---|---|
| 4,815,479 | A * | 3/1989 | Carr | 607/102 |
| 5,176,146 | A * | 1/1993 | Chive et al. | 600/549 |
| 5,912,179 | A * | 6/1999 | Alvarez et al. | 436/63 |
| 5,949,845 | A | 9/1999 | Sterzer | |
| 6,061,589 | A * | 5/2000 | Bridges et al. | 600/430 |
| 6,463,336 | B1 | 10/2002 | Mawhinney | |
| 6,773,159 | B2 * | 8/2004 | Kim et al. | 374/122 |
| 7,561,908 | B2 * | 7/2009 | Glukhovsky et al. | 600/407 |
| 7,769,469 | B2 * | 8/2010 | Carr et al. | 607/101 |
| 8,044,843 | B2 * | 10/2011 | Baath | 342/124 |
| 2003/0088180 | A1 * | 5/2003 | Van Veen et al. | 600/430 |
| 2006/0241410 | A1 * | 10/2006 | Fang et al. | 600/430 |
| 2007/0093702 | A1 * | 4/2007 | Yu et al. | 600/326 |
| 2010/0152591 | A1 * | 6/2010 | Yu et al. | 600/481 |

OTHER PUBLICATIONS

Lazebnik, Mariya, et al. "Tissue-mimicking phantom materials for narrowband and ultrawideband microwave applications" Physics in Medicine and Biology (2005) Aug. 31, 2005 pp. 4245-4258.
Sterzer, F. "Microwave Radiometers for Non-Invasive Measurements of Subsurface Tissue Temperatures" Automedica, 1987, vol. 8.pp. 203-211, Apr. 1987.
Mendecki, Jozef, et al. "Microwave Applicators for Localized Hyperthermia Treatment of Cancer of the Prostrate" Int. I Radiation Oncology Biol. Phys. vol. 6 pp. 1583-1588, Jun. 10, 1980.
Sterzer, Fred, et al. "Microwave Treatments for Prostate Disease" IEEE Transaction on Microwave Theory and Techniques, vol. 48, No. 11, Nov. 2000 pp. 1885-1891.

* cited by examiner

*Primary Examiner* — Jonathan Cwern
*Assistant Examiner* — Shahdeep Mohammed
(74) *Attorney, Agent, or Firm* — Moser Taboada (57) ABSTRACT

Provided among other things is a thermal noise imaging device with (a) thermal noise source; (b) amplifier of thermal noise; (c) antennas adapted to transmit the amplified noise to a perfused body and receive perfused body noise; (d) reference circuit adapted to receive the amplified thermal noise and produce a reference signal; (e) perfused body docking interface adapted to interface with one or more surfaces of the perfused body and (i) support a reflection set of one or more antennas in close proximity with a surface of the perfused body or (ii) support separate transmission sets of one or more antennas on opposing surfaces of the perfused body; and (f) analytical module for the perfused body noise and the reference signal and determining a reflected power from the reflection set or a transmitted power from the transmission sets.

22 Claims, 7 Drawing Sheets

DIAGNOSTIC DEVICES USING THERMAL NOISE

Embodiments of the present invention generally relate to devices and methods for detecting anomalies in biological tissue or other perfused bodies using amplified thermal noise.

Any object at any temperature is known to emit radiation. This radiation is usually referred to as thermal radiation. The characteristics of this radiation depend on the temperature and properties of the object. The intensity of this thermally generated radiation is given by Planck's famous black body radiation formula that for microwave frequencies simplifies to the Raleigh-Jeans's formula, which states that the intensity of the microwave radiation is proportional to the absolute temperature and the emissivity of the object. If the variations of emissivity with temperature are small, as in the case of tissues it follows that that the microwave power emitted from tissues is directly proportional to their absolute temperature. [See article by one of the present inventors, Fred Sterzer, "Microwave Radiometers for Non-Invasive Measurements of Subsurface Tissue Temperatures", *Automedica*, 1987, Vol. 8, pages 203-211]. Medical microwave radiometers are instruments that can measure the thermally generated microwave noise emissions from subsurface tissues, and then relate these measurements to the temperatures of these tissues. Such radiometers, which are well known in the art, can non-invasively measure subsurface tissues temperatures to a depth of several centimeters.

This application describes novel uses of microwave medical radiometers and similar radiometers. One of the novel modes of using medical radiometers described in this application is to use them as receivers of amplified thermal noise that is reflected from tissues that are illuminated with amplified noise (active diagnostic radiometry). When operated in the active mode the radiometers measure the relative amounts of blood in tissues, i.e. amount of vascularization of tissues. The amplified noise powers used in the active mode can be orders of magnitude below any existing safety standard for exposure to radiofrequencies or microwaves because microwave radiometers are ultra-sensitive microwave receivers. No ionizing radiation is used. Medical applications of this reflection mode range from detecting subsurface cancers to imaging (scanning) of wounds and burns.

The advantages of using amplified microwave noise rather than single microwave frequencies to measure tissue properties can include:

The same microwave radiometer using the same antennas can be used for both non-invasively measuring tissue temperatures (passive mode) and as an ultra-sensitive receiver of amplified noise for non-invasively measuring tissue properties (active mode). As a result tissue temperatures and tissue properties are automatically measured for the same volume of tissues.

The use of wideband noise sharply reduces or completely eliminates artifacts such as resonances, reflections, diffraction which can cause erroneous readings when using single frequencies.

In the active diagnostic mode, where thermal noise is broadcast into tissues the amount of thermal noise power density that is broadcast is orders of magnitude below any existing safety standard for exposure to radiofrequencies or microwaves. Use of this mode is therefore safe. No ionizing radiation is used.

A second novel diagnostic mode of using medical radiometers described in this application is to use them as receivers of amplified thermal noise that is transmitted through tissues that are illuminated with amplified noise. In this mode the amount of noise power that is transmitted through the tissues is inversely proportional to the blood content of the traversed tissues. This mode is, for example, useful for detecting cancer lesions such as breast cancer lesions since breast cancer lesions are more vascularized than fatty breast tissues, for interrogating organs such as the detection of fluids in the lungs of neonatal or infants where the use of ionizing radiation is not allowed. In this mode, just as in the diagnostic reflection mode, the thermal noise power density that is broadcast into patients can be held well below any existing safety standard for exposure to radiofrequencies or microwaves.

In a therapeutic medical mode, tissues are heated with high-power amplified thermal noise power and the temperatures of the heated tissues are monitored with a medical radiometer operating in the passive mode. Typical applications are hyperthermia treatments of cancer. Advantages of this therapeutic mode are that when the same antenna can be used for both heating and temperature measurements, both cover the same volume of tissues, and that resonances, reflections, diffraction effects are minimized, effects that can cause dangerous hotspots when single frequencies are used for heating.

Non-medical applications of radiometers using amplified thermal noise include for example the inspection of food and industrial and home cooking [Is the food sufficiently cooked and still moist?], airport security [e.g., lie detection—measuring changes in blood perfusion of the frontal cortex during questioning; has the person fever? does the person carry objects with microwave properties different from that of tissues or normal clothing?]; fitting of shoes, and the like

SUMMARY

Embodiments of the present invention generally relate to . . . .

Provided among other things is a thermal noise imaging device comprising: (a) a source of thermal noise; (b) an amplifier for amplifying the thermal noise; (c) one or more antennas adapted to transmit the amplified thermal noise to a perfused body and receive perfused body noise, which is the amplified thermal noise after reflection from or transmission through the perfused body; (d) a reference circuit adapted to receive the amplified thermal noise and produce a reference signal; (e) a perfused body docking interface adapted to interface with one or more surfaces of the perfused body and (i) support a reflection set of one or more antennas in close proximity with a surface of the perfused body or (ii) support separate transmission sets of one or more antennas on opposing surfaces of the perfused body; and (f) an analytical module for receiving the perfused body noise and the reference signal and determining one or more of a reflected power from the reflection set and a transmitted power from the transmission sets.

Further provided is a thermal noise imaging method comprising: (1) transmitting amplified thermal noise to a perfused body; (2) receiving perfused body noise, which is the amplified thermal noise after reflection from or transmission through the perfused body; (3) producing a reference signal from the amplified thermal noise; and (4) from the perfused body noise and the reference signal determining one or more of a reflected power and a transmitted power.

The thermal noise imaging device can further comprise a positional emitting/receiving device in register with antennas, and the method can comprise operating the same. The TNI device and the method can be such that the positional emitting/receiving device comprises: an x-ray source; and an x-ray detector, the x-ray source and x-ray detector. The TNI device can be used in conjunction with opposing transmission sets of antennas, each set of which can be used as a reflection set. The method can comprise determining transmitted power, and/or determining reflected power. One or more of the antennas can be used to receive native thermal noise from the perfused body, and the analytical module (or the method) is operable to determine a perfused body temperature from such native thermal noise. The perfused body docking interface can comprise a compressor for compressing the perfused body (e.g., breast tissue) comprising two opposing plates, wherein the device can comprise opposing transmission sets of antennas positioned respectively on the opposing plates. The method can comprise compressing the body, and measuring transmitted power. The perfused body docking interface can comprise a neonatal support and a thoracic plate, wherein the device can comprise opposing transmission sets of antennas positioned respectively on a neonatal support and a thoracic plate. The reflection sets or the transmission sets can comprise antennas in a number and with a spacing allowing directional transmission and reception as a phased array, and wherein the device can comprise a controller that variably controls the timing of transmission and reception at the antennas to provide a range of directionalities, and the method can transmit and/or receive via a phased array. The device can comprise a controller that operates the reflection sets or the transmission sets to transmit thermal noise into the perfused body to heat the perfused body or a portion thereof, and the method can comprise transmitting thermal noise to heat the perfused body or a portion thereof. The reflection sets or the transmission sets can comprise antennas in a number and with a spacing allowing directional transmission as a phased array, wherein the device can comprise a controller that variably controls the timing of transmission at the antennas to provide a range of directionalities. The method can comprise utilizing phased arrays to heat with a range of directionalities. One or more of the antennas can be used to receive native thermal noise from the perfused body, and the analytical module can be operable to determine a perfused body temperature from such native thermal noise. The method can comprise receiving such thermal noise and determining a temperature.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

Tissue modeling phantoms have been used to demonstrate, by way of illustration, that the thermal noise imaging device ("TNI device") of the invention can detect very small simulated tumors situated inside a model for normal fatty breast tissues. This sensitivity is believed to be a function of thermal noise to distinguish the typically blood rich, and hence water rich, tumor from the background of fatty tissue. In certain embodiments, the device can operate in a more passive mode where the antennas pick up native thermal noise and determine a temperature from the received native thermal noise. "Native" thermal noise refers to thermal noise due to the heat of the tissue and the characteristics of the tissue for emitting thermal noise in response to heat; it does not include reflected, refracted, diffracted or transmitted thermal noise from an tissue-external electronic device. It may be that thermal noise received in a mode seeking native thermal noise includes some thermal noise from adjacent tissues or structures, but such thermal noise can be dealt with by calibration techniques or the like.

The TNI device can be used to make such measurements with any "perfused body," which is any body whose state (e.g., health, size) is dependent on or measurable by the amount or distribution of aqueous liquid within the body (perfused, infused, or otherwise). Such a body can be fitted to or aligned with the TNI device. It may be that in one state the perfused body has little or no aqueous liquid, so long as there is a state of the body that has aqueous liquid. An animal tissue is a perfused body.

In certain embodiments, the TNI device can be operated to heat tissue or a portion thereof. Such heating can be to provide relatively benign therapeutic heating, or to seek to selectively injure non-desired tissue such as tumors. Since such heating can operate with the same antennas as used for imaging, these antennas are then well positioned for imaging the effects of such heating, such as increased or reduced blood flow. A temperature monitoring mode for the TNI device can also use the antennas for determining temperature changes in response to such heating. Such imaging or heat monitoring can be used in a feedback mode to determine the time or power devoted to the heating operation. The heating operation may function iteratively, such as period x beginning every period y, with the period x and the power used in period x varied in response to the monitoring activated in the previous interim after period x but before the end of period y.

In one embodiment, the amplified noise is in the frequency range of about 3.7 GHz to about 4.2 GHz. This frequency range can be used for operation in the passive mode when shielding from interfering terrestrial microwave emissions is cumbersome. This is because the Federal Communications Commission forbids terrestrial emissions in the 3.7 GHz to 4.2 GHz frequency range. This consideration does usually not apply when only amplified thermal noise (active mode) is employed, the amplified noise usually being larger than any interfering terrestrial emissions.

The allowed exposure limit of individuals to microwaves in the 3.7 GHz to 4.2 GHz frequency range for example is typically 10 milliwatts per square centimeter (+10 dBm/cm squared). In the diagnostic modes the amplified thermal noise power density can be several orders of magnitude below any safety standard.

Note that the TNI devices, which can operate over a bandwidth for example of 500 MHz, are able to accurately measure the power of thermal noise that is not amplified (≈−85 dBm). Thus, losses of 50 dB in tissues or even higher can be overcome by using high-gain amplifiers in the thermal noise source without ever approaching existing safety standards for exposure.

Thermal noise sources that can be amplified for use in the invention include, for example, solid-state noise diodes, fluorescent bulbs matched to microwave transmission lines, or heated resistors.

Those of skill will recognize a wealth of uses for the device of the invention. These include, for example, providing simple and rapid indications of whether anticancer treatments such as chemotherapy, radiation therapy, hyperthermia, hypothermia, or thermal ablation have been effective in treating subcutaneous solid malignant tumors. For example, the TNI device can provide indications that blood flow has changed, that local temperature has changed, or that an ablating temperature has been achieved for an appropriate period of time. The TNI device can be used, for example, to detect tumors through variations in transmitted or reflected thermal noise. The TNI device can further be used, for example, to detect fluid buildups. For example, it can be used to detect pulmonary edema, such as in neonatal infants. While healthy lungs are nearly transparent to amplified thermal noise since they are filled with air, water is highly absorbent of thermal noise and there will also be large reflection of thermal noise from the air-water interface. The result is very large changes in transmission or reflection of amplified thermal noise. Similarly, changes in perfusion can be detected, such as in the frontal cortex in response to factors such as drugs, emotional stress, and the like.

While the invention is not limited to such, favorable tissues for imaging include those for which normal tissue is relatively uniform or transparent to the relevant thermal noise. Similarly, tissues that can be imaged via relatively short pathways for the amplified thermal noise are favorably utilized.

Figure 1:
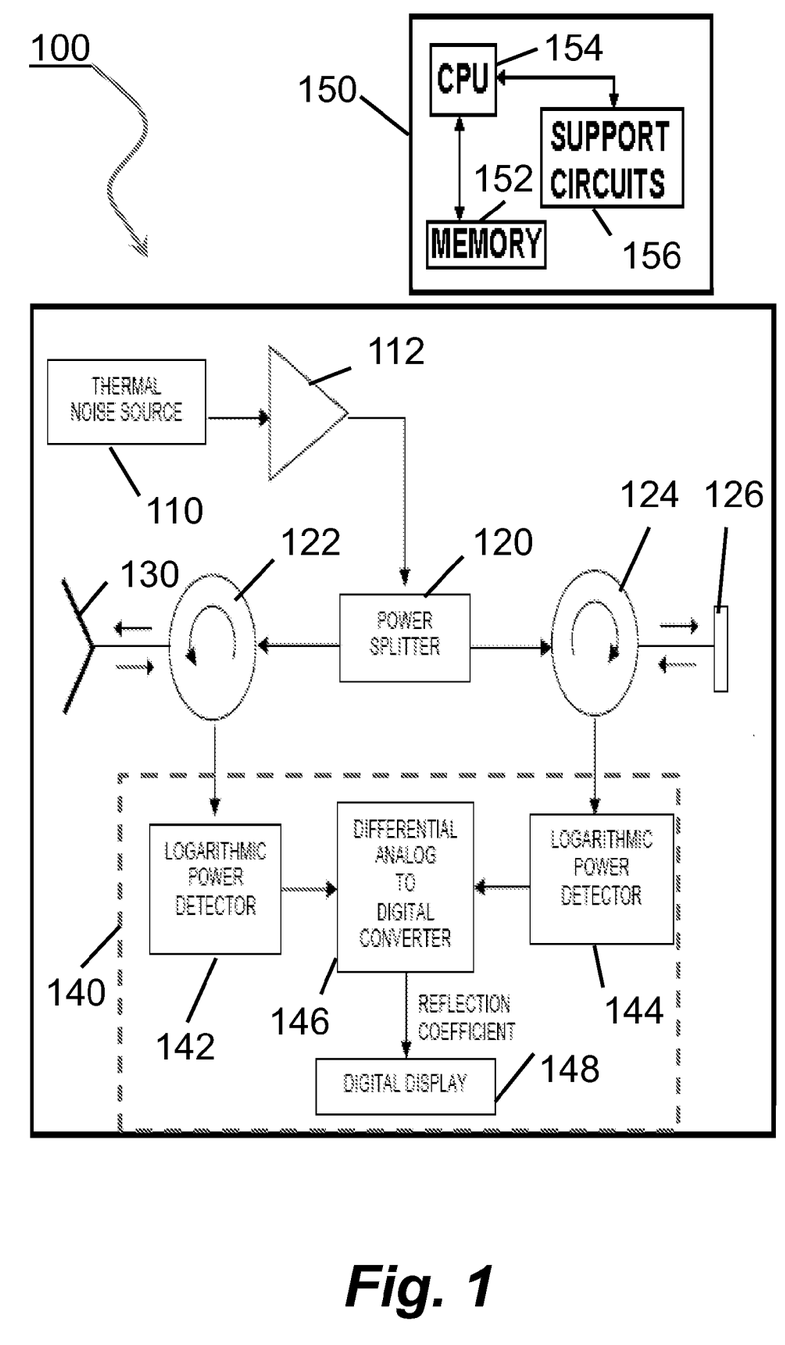
FIG. 1 shows an illustrative schematic for a thermal noise imaging device as used for measuring reflected thermal noise.

FIG. 1 shows an illustrative schematic for an embodiment of a thermal noise imaging device ("TNI device 100") as used for measuring reflected thermal noise. The device 100 includes a thermal noise source 110, an amplifier 112, a power splitter 120, an output circulator 122, a reference circulator 124, and an analytical module 140. The analytical module 140 can include a logarithmic power detector 142, a logarithmic power detector 144, and a differential analog-to-digital (A/D) converter 146. The analytical module 140 may be coupled to a controller 150 and a display 148, such as a digital display.

The thermal noise source 110 is configured to provide radio frequency (RF) radiation to an input of the amplifier 112. The thermal noise source 110 can provide RF radiation in the microwave region. In an exemplary non-limiting embodiment, the thermal noise source 110 can provide microwave radiation having a frequency between 3.7 and 4.2 GHz. The RF radiation can be characterized as thermal noise (also referred to as Johnson noise or Nyquist noise) and can be generated using known techniques and circuitry. An output of the amplifier 112 can provide for example amplified thermal noise power of about −20 dBm.

The amplified thermal noise provided by the amplifier 112 is coupled to an input of the power splitter 120. The power splitter 120 includes an output coupled to an input of the output circulator 122, and an output coupled to an input of the reference circulator 124. The power splitter 120 is configured to divide power of the amplified thermal noise in half such that half or approximately half of the power is provided to the output circulator 122 and the remaining power (half or approximately half) is provided to the reference circulator 124. The output circulator 122 provides the RF radiation from the power splitter 120 to an antenna 130. The antenna 130 radiates the RF radiation ("output RF").

The antenna 130 also receives RF radiation, which a reflected portion of the output RF radiation (e.g., reflected from tissue) ("input RF"). The antenna 130 provides the input RF to the output circulator 122. The output circulator 122 provides the input RF to the logarithmic power detector 142. The logarithmic power detector 142 provides an analog signal indicative of the power of the input RF to the differential A/D converter 146.

The reference circulator 124 provides the RF radiation from the power splitter 120 to an RF termination 126. RF radiation reflected by the termination 126 ("reflected RF") is received by the reference circulator 124 and provided to the logarithmic power detector 144. The logarithmic power detector 144 provides an analog signal indicative of the power of the reflected RF to the differential A/D converter 146.

The differential A/D converter 146 generates digital samples of the difference of the analog signals from the logarithmic power detectors 142 and 144 ("reflection coefficient"). The reflection coefficient can be provided to the display 148. The display 148 can show an indication of the reflection coefficient. The reflection coefficient provides an indication of the power of the RF radiation reflected from the tissue as compared to the generated RF radiation by the thermal noise source 110.

The controller 150 comprises a central processing unit (CPU) 154, a memory 152, and support circuits 156 for the CPU 154 and is coupled to and controls one or more of the various elements of the TNI device 100 or, alternatively, via computers (or controllers) associated with TNI device 100. The controller 150 may be one of any form of general-purpose computer processor that can be used for controlling various devices and sub-processors. The memory, or computer-readable medium, 152 of the CPU 154 may be one or more of readily available memory such as random access memory (RAM), read only memory (ROM), flash memory, floppy disk, hard disk, or any other form of digital storage, local or remote. The support circuits 156 are coupled to the CPU 154 for supporting the processor in a conventional manner. These circuits can include cache, power supplies, clock circuits, input/output circuitry and subsystems, and the like. Methods of operating the TNI device 100 may be stored in the memory 152 as software routine that may be executed or invoked to control the operation of the TNI device 100, such as activating the analytical module 140, processing the reflection coefficient, outputting to the display 148, and the like. The software routine may also be stored and/or executed by a second CPU (not shown) that is remotely located from the hardware being controlled by the CPU 154.

Figure 2:
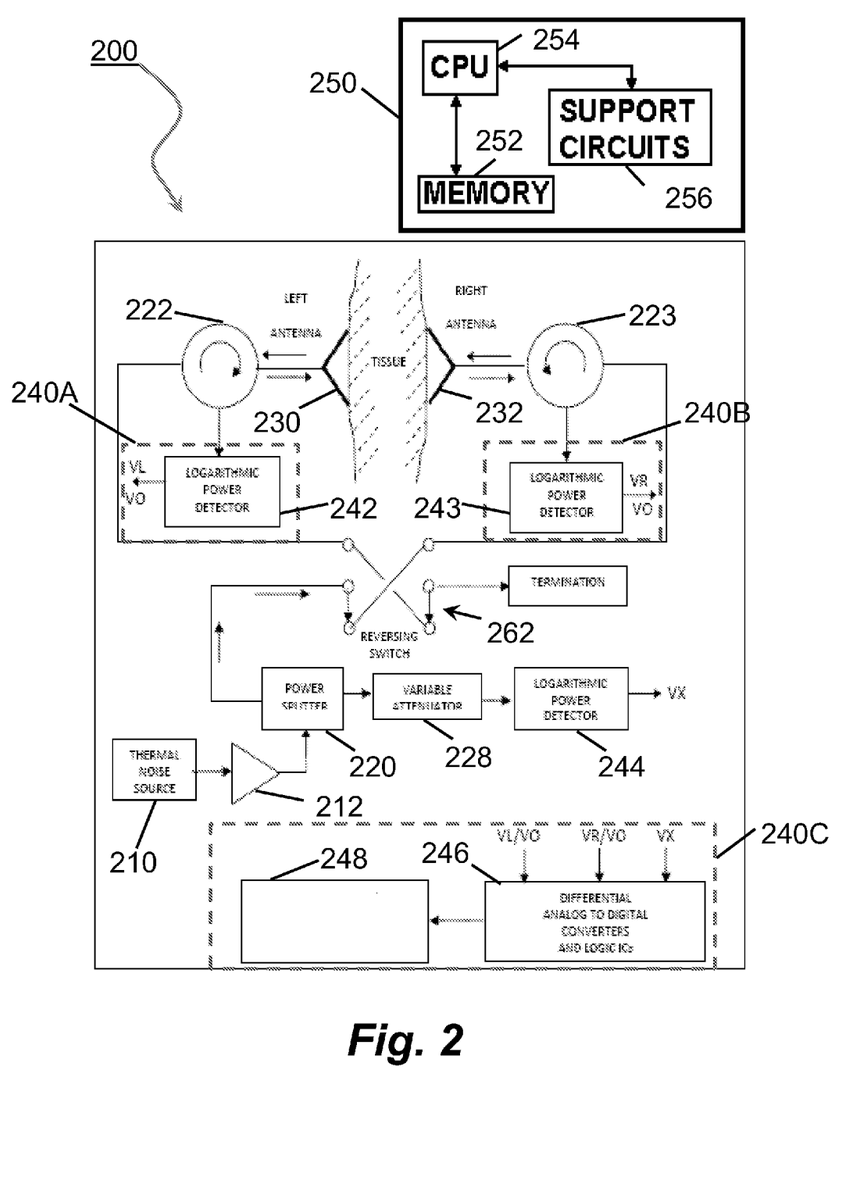
FIG. 2 shows an illustrative schematic for a thermal noise imaging device as used for measuring transmitted thermal noise.

FIG. 2 shows an illustrative schematic for an embodiment of a thermal noise imaging device ("TNI device 200") as used for measuring reflected thermal noise. The TNI device 200 includes a thermal noise source 210, an amplifier 212, a power splitter 220, a variable attenuator 228, a logarithmic power detector 244, an RF termination 260, a reversing switch 262, a left circulator 222, a right circulator 223, and an analytical module 240. The analytical module 240 comprises portions 240A through 240C and includes a logarithmic power detector 142, a logarithmic power detector 143, and a differential A/D converter 246. The analytical module 240 can be coupled to a display 248 and/or a controller 250.

The thermal noise source 210 is configured to provide RF radiation to an input of the amplifier 212. The thermal noise source 210 can provide RF radiation in the microwave region. In an exemplary non-limiting embodiment, the thermal noise source 210 can provide microwave radiation having a frequency between 3.7 and 4.2 GHz. The RF radiation can be characterized as thermal noise (also referred to as Johnson noise or Nyquist noise) and can be generated using known techniques and circuitry. An output of the amplifier 212 can provide for example amplified thermal noise power of about −20 dBm.

The amplified thermal noise provided by the amplifier 212 is coupled to an input of the power splitter 220. The power splitter 220 includes an output coupled to an input of the reversing switch 262, and an output coupled to an input of the variable attenuator 228. The power splitter 220 is configured to divide power of the amplified thermal noise in half such that half or approximately half of the power is provided to the reversing switch 262 and the remaining power (half or approximately half) is provided to the variable attenuator 228. The variable attenuator 228 attenuates the RF radiation from the power splitter and provides the attenuated RF radiation to the logarithmic power detector 244. The amount of attenuation of the variable attenuator 228 can be adjusted to equal the path loss to the antennas coupled to the left and right circulators 222 and 223. The logarithmic power detector 244 measures the power of the attenuated RF radiation and provides an analog signal referred to as "VX".

The reversing switch 262 includes four ports, one coupled to the power splitter 220, one coupled to the RF termination 260, one coupled to the left circulator 222, and one coupled to the right circulator 223. The reversing switch 262 includes two positions: in a first position, the RF radiation from the power splitter 220 is provided to the right circulator 223 and the left circulator 222 is coupled to the RF termination 260; in a second position, the RF radiation from the power splitter 220 is provided to the left circulator 222 and the right circulator 223 is coupled to the RF termination 260.

When the reversing switch 262 provides RF radiation to the right circulator 223 (i.e., first position), the right circulator 223 provides the RF radiation to a right antenna 231. A left antenna 230 receives at least a portion of the RF radiation (e.g., after being transmitted through tissue). The left antenna 230 provides the received RF radiation to the left circulator 222. The left circulator 222 provides the received RF radiation to the logarithmic power detector 242. The logarithmic power detector 242 measures the power of the received RF radiation and provides a signal "VO". The right antenna 231 also receives reflected RF radiation due to any mismatch between the right and left antennas 230 and 231. The reflected RF radiation is provided to the logarithmic power detector 243 through the right circulator 223 and measured to produce a mismatch value "VR".

When the reversing switch 262 provides RF radiation to the left circulator 222 (i.e., second position), the left circulator 222 provides the RF radiation to the left antenna 230. The right antenna 231 receives at least a portion of the RF radiation (e.g., after being transmitted through tissue). The right antenna 231 provides the received RF radiation to the right circulator 223. The right circulator 223 provides the received RF radiation to the logarithmic power detector 243. The logarithmic power detector 243 measures the power of the received RF radiation and provides a signal "VO". The left antenna 230 also receives reflected RF radiation due to any mismatch between the right and left antennas 230 and 231. The reflected RF radiation is provided to the logarithmic power detector 242 through the left circulator 222 and measured to produce a mismatch value "VL".

The VX, VL/VO, and VR/VO signals are provided to the differential A/D converter 246. Both values of VO (from the left and right antennas 230 and 231) should be the same, but the VL and VR values can differ, since the tissue (e.g., the thorax of a neonate that the antennas 230 and 231 are in contact with are likely to have different characteristics. Since two VL/VO and VR/VO measurements are made at different times, the differential A/D stores the two measurements. The differential A/D converter 246 generates digital samples of the difference of the VR/VO signal and the VL/VO signal ("reflection coefficient"). The reflection coefficient can be provided to the display 248. The display 248 can show an indication of the reflection coefficient. The reflection coefficient provides an indication of the power of the RF radiation transmitted through the tissue as compared to the generated RF radiation by the thermal noise source 210.

The controller 250 comprises a central processing unit (CPU) 254, a memory 252, and support circuits 256 for the CPU 254 and is coupled to and controls one or more of the various elements of the TNI device 200 or, alternatively, via computers (or controllers) associated with TNI device 200. The controller 250 may be one of any form of general-purpose computer processor that can be used for controlling various devices and sub-processors. The memory, or computer-readable medium, 252 of the CPU 254 may be one or more of readily available memory such as random access memory (RAM), read only memory (ROM), flash memory, floppy disk, hard disk, or any other form of digital storage, local or remote. The support circuits 256 are coupled to the CPU 254 for supporting the processor in a conventional manner. These circuits can include cache, power supplies, clock circuits, input/output circuitry and subsystems, and the like. Methods of operating the TNI device 200 may be stored in the memory 252 as software routine that may be executed or invoked to control the operation of the TNI device 200, such as activating the analytical module 240, processing the reflection coefficient, outputting to the display 248, and the like. The software routine may also be stored and/or executed by a second CPU (not shown) that is remotely located from the hardware being controlled by the CPU 254.

There can be an array of reflection antennas 130, or of transmission antennas 230. Those of skill will recognize that switches and other components can be provided such that transmission antennas can be operated as reflection antennas. Phased arrays antennas are widely used in many communications and defense applications as well as in radio astronomy using low frequency and microwave radiometers. Transmit or receive patterns of such arrays can be shaped and directed electronically. Phased array antennas are also used in medical applications such as in ultrasonography for medical imaging.

Electronically steered receive phased array antennas consist of a group of antennas in which the relative phases of the received signals by each antenna can be electronically varied in such a way that effective receive pattern of the array is reinforced in the desired directions and suppressed in the undesired directions (Skolnik, M., (1990) *Radar Handbook*, Second Edition, McGraw-Hill, Inc. New York). Such phased arrays can produce a number of different antenna patterns including sharp pencil beams that can be pointed in different directions, and very wide beams that cover large areas close to the antennas. The relations between antenna patterns and the thermal noise received by these antennas from bodies that are at non-uniform temperatures is given in (Pierce J R, "The General Source of Noise in Vacuum Tubes", *IRE Trans*. Vol. ED-1, pp. 134-167, December 1954.). These relations make it possible to obtain the temperature distributions in tissues from knowledge of the noise received form varying beam patterns in the tissues by solving the "inverse problem", a problem familiar from the image reconstruction in CAT scans. Solving the inverse problem for radiometers is retrieving temperature distributions in tissues consistent with the measured radiometer temperature data (Mizushina S, Shimizu T, Suzuki K, Kinomura M, Ohba H, Sugiura T (1993) Retrieval of temperature-depth profiles in biological objects from multi-frequency microwave radiometric data. *J Electr Waves & Appl* 7: 1515-480). The same electronically steered arrays used as transmit arrays can steer the amplified thermal noise Phases can be controlled with electronic phase shifters and the data taken can be automatically digitized and fed into a electronic processor. As appropriately programmed, the electronic processor can command the varying of the relative phase shifts of the array antennas to accomplish specific task as commanded such as "locate and display all burns in the tissue being examined", or "scan the antenna beams over the tissues under examination, solve the inverse problem, and display the three-dimensional tissue temperature profile".

The aiming in emission or reception achieved with operating an array of antennas as a phased array are available even though the electromagnetic signal is not coherent, but this use does impose some limits on band width. The phased array format is generally available with a bandwidth of 500 MHz. The effectiveness of larger bandwidths can be determined (such as empirically), for instance for given context of use.

Antennas can be fabricated to conform to normally encountered tissues surfaces. Antennas with different geometries and apertures can be designed and fabricated, such as spiral and X-slot microstrip antennas, a type of microstrip antennas that Applicants have successfully used with passive radiometers. Antennas with large apertures can, for example, interrogate small volumes of tissues, since the effective gain of antennas is approximately proportional to the square of the apertures in either reflection or transmission mode. Example spiral antennas are described in more detail, for example, in U.S. Pat. No. 6,463,336.

For use in confined spaces, such as spaces accessed by catheters small diameter antennas may be of coaxial gap or helical designs and can, for example, be used in the urethra. [See for example F. Sterzer et al, "Microwave Treatments for Prostate Disease", IEEE Trans. MTT, 48, 11, Nov. 2000]. Coaxial antennas can be designed to emit and receive in one preferred direction. [See for example J. Mendecki et al, "Microwave Applicators for Localized Hyperthermia Treatment of Cancer of the Prostate", Int. J. Radiation Oncology Biol. Phys. Vol. 6, 1980]. By rotating such directional antennas in the urethra the angular position of prostate lesions can be determined. Such antennas can be used in reflection mode to make measurements of tissue adjacent to such confined spaces, such as to search for abnormal reflections (possibly prostate tumors) adjacent to the urethra. Or, such antennas can be paired with antennas external to the subject's body for use in transmission mode.

Subjects for diagnostics and therapies using the TNI device can include, for example, animals, which can be mammals such as humans. Specific organs can, in some cases be isolated by appropriate external placement of the antennas and appropriate manipulation of the subject. Isolation can be by use of antennas inserted in the body by catheter or by endoscopic techniques, which methods may or may not use external antennas in conjunction with the inserted antennas.

In certain embodiments, low-voltage power supplies power the circuitry. The AC line voltages that power the power supplies will generally be isolated in accordance with FDA safety standards for medical devices. Generally, the housings of the patient contacting TNI device components, including the antennas, will be covered with dielectrics to insure that no metallic parts can touch a human subject. Similar precautions can be taken with the noise source.

Tissue equivalent phantoms for various parts of the human body can be designed and fabricated with means for varying the perfusion of phantom blood by following published recipes. See, e.g., Lazebnik M et al (2005), "Tissue-mimicking phantom materials for narrowband and ultrawideband microwave applications", *Phys. Med. Biol.*, 50, 4245-4258. (2005). Measured data for a variety of tissue equivalent phantom configurations with various levels of blood perfusion and for various antennas can be catalogued, and such data can be assembled in a form that aids in the interpretation of reflection and transmission of amplified noise.

Figure 6A:
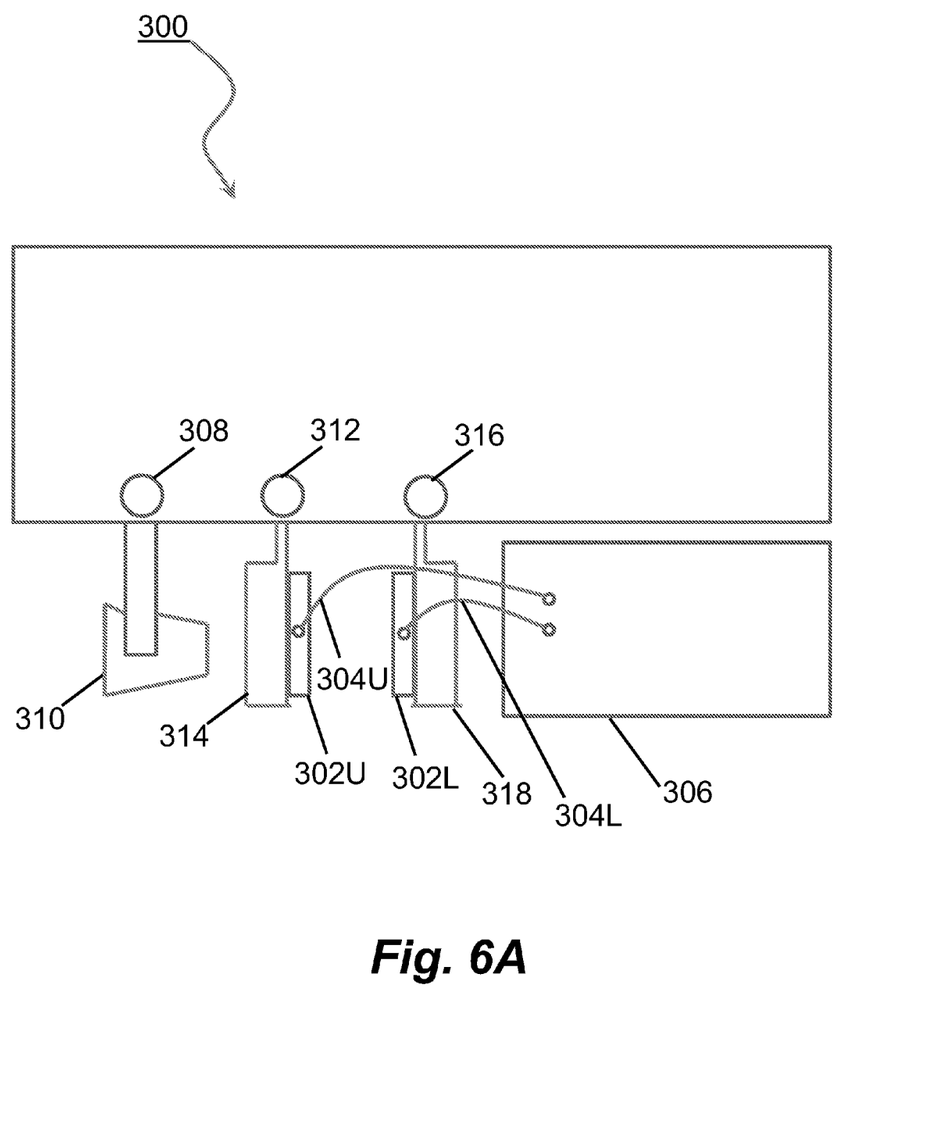
FIGS. 6A and 6B show mammography equipment with an incorporated thermal imaging device.
Figure 6B:
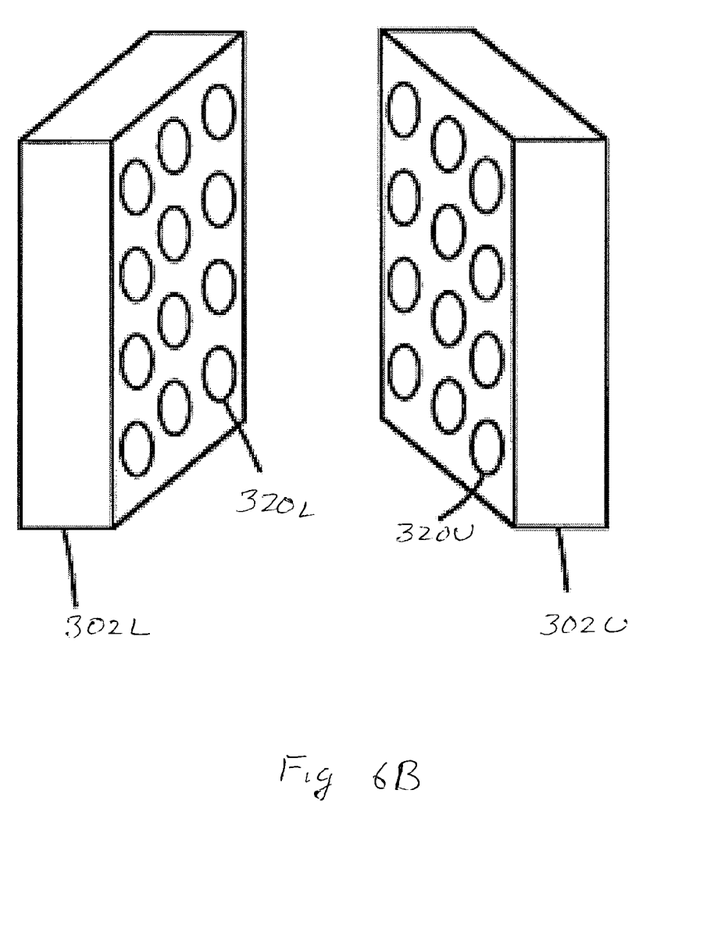
Figure 7:
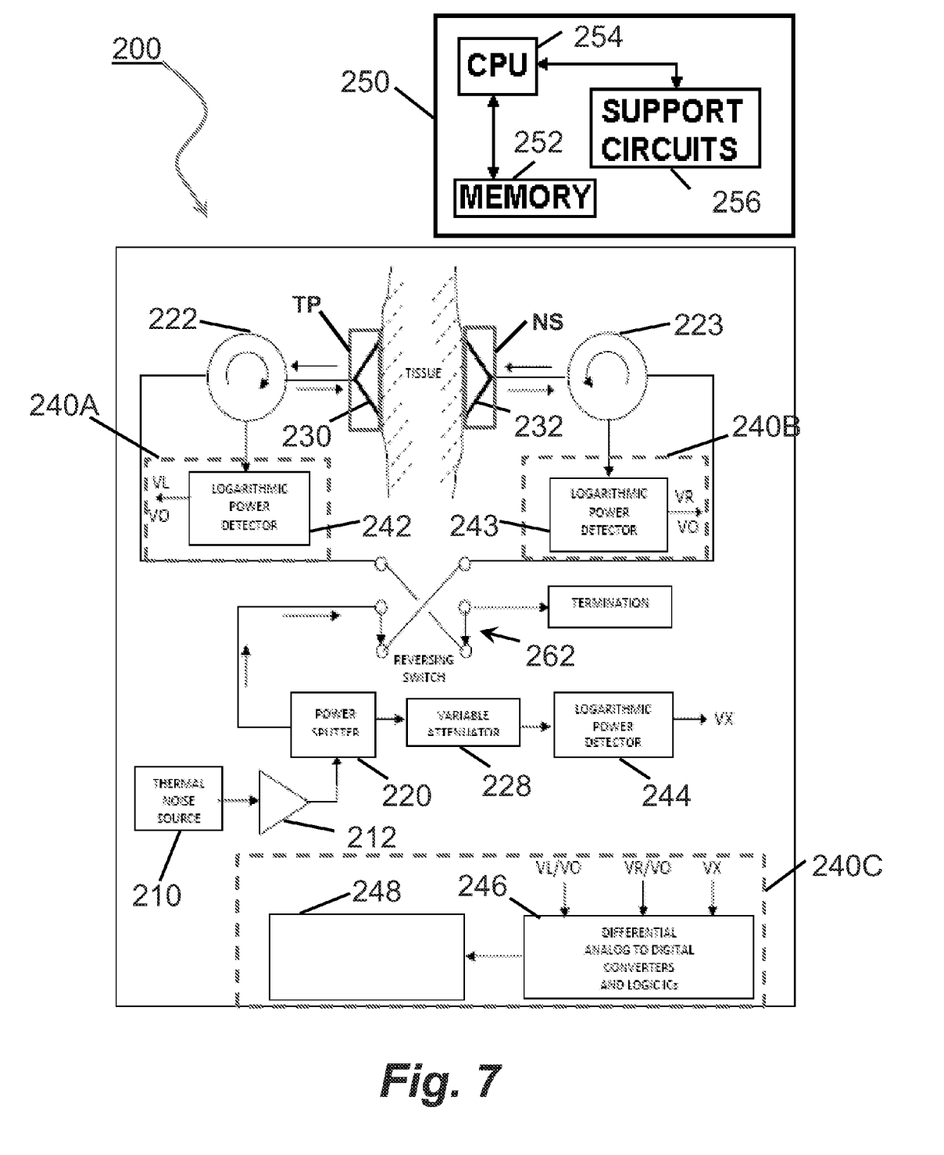
FIG. 7 shows a version of the device of FIG. 2 with a neonatal support NS and a thoracic plate TP.

A tissue docking interface can be illustrated with mammography equipment, as is known in the art for taking an X-ray images of a patient's breast for use by a radiologist in identifying and locating a cancerous lesion in the breast. FIG. 6A shows a combination of conventional mammography equipment 300 in combination with the TNI device, that comprises upper and lower antenna stages 302U and 302L (shown in more detail in FIG. 6a) coupled by cables 304U and 304L to TNI electronics 306. ("U" and "L" are for upper and lower, respectively, but other orientations that compress the breast and position the X-ray tube and antennas will be apparent to those of skill in the art.)

Mammography equipment 300 comprises X-ray adjustment 308 for adjusting the position of X-ray tube 310, adjustment 312 for adjusting the position of positioning guide 314 and adjustment 316 for adjusting the position of detector 318 (which can be a film holder). In operation, a patient's breast is placed between positioning guide 314 and detector 318, which are adjusted by technicians to compress the breast therebetween in a manner that minimizes the chance of metastasis of any cancerous lesion which may be present taking place.

45 As shown in FIG. 6A, upper antenna stage 302U is attached to the bottom of positioning guide 314 and lower antenna stage 302L is attached to the top of film holder 318, so that, with such attachments, the patient's breast is lightly compressed between upper antenna stage 302U and lower antenna stage 302L. As shown in FIG. 6B, a 2-dimensional upper array of radiometer antennas 320U can be attached to the bottom surface of upper antenna stage 302U, and a corresponding 2-dimensional lower array of radiometer antennas 320L can be attached to the top surface of lower antenna stage 302L. Thus, while the patient's breast is compressed, each of radiometer antennas 320U of the upper array is in direct contact with one side of the patient's breast and each of radiometer antennas 320L of the lower array 320L is in direct contact with the opposite side of the patient's breast. X-rays and microwave images can be taken sequentially. The X-ray film cassettes can be removed and replaced by the microwave equipment.

The cooperative combination of the TNI device with mammograph equipment 300 has at least two advantages. First, the correspondence in the location within the breast of the spatial position of the cancerous lesion is insured because the lightly compressed breast remains immobile during the occurrence of both the X-ray procedures, and during the procedures available with the TNI device. Second, since all procedures take place in the same time frame, the breast need be compressed only once. This greatly reduces the chance of pressure/manipulation induced metastasis.

The concept that the antenna(s) of a TNI device and the energy emitters and/or receivers of another imaging device or an energy emitting device (together "positional emitting/receiving" devices) are in "register" means that they are in fixed or calibrated physical relation to one another such that the imaging or transmission data from one can be correlated in at least one dimension with that from the other. Such other imaging devices include for example fluoroscopy devices, CT scanners, MRI devices, nuclear medicine imaging devices (such as PET scan devices), ultrasound devices, interventional radiology devices, and the like. Such other energy emitting devices include for example devices for reducing or ablating diseased tissue, such a radiation treatment devices (such as using high-energy x-rays, proton beams, or other types of radiation), high-intensity focused ultrasound, and the like.

Other tissue docking interfaces can include for example a neonatal support (adapted to support a neonate) and a thoracic plate (adapted to fit over the thorax of a neonate), where the device comprises opposing transmission sets of antennas positioned respectively on the neonatal support and the thoracic plate. Further tissue docking interfaces can include for example molded devices for interacting the antennas with specific parts of an animal body, such as necks, elbows, upper arms, wrists, hands, thighs, knees, calfs, ankles, feet, scrotums, and the like. Such animal-part specific fittings can include antennas and quick release components for connecting the antennas to appropriate electronics. Such animal-part specific fittings can further include docking or alignment elements for registering the emitting and/or receiving elements of positional emitting/receiving devices. Docking elements can be, for example, male/female interacting parts, clips, clamps, and the like. Alignment elements can be for example notches, markings, more loosely interacting male/female parts, and the like.

The concept that the antenna(s) of a TNI device and the energy emitters and/or receivers of another imaging device are in "register" means that they are in fixed or calibrated physical relation to one another such that the imaging data from one can be correlated in at least one dimension with that from the other.

Example 1

Reflections From Oil/Saline

Figure 3:
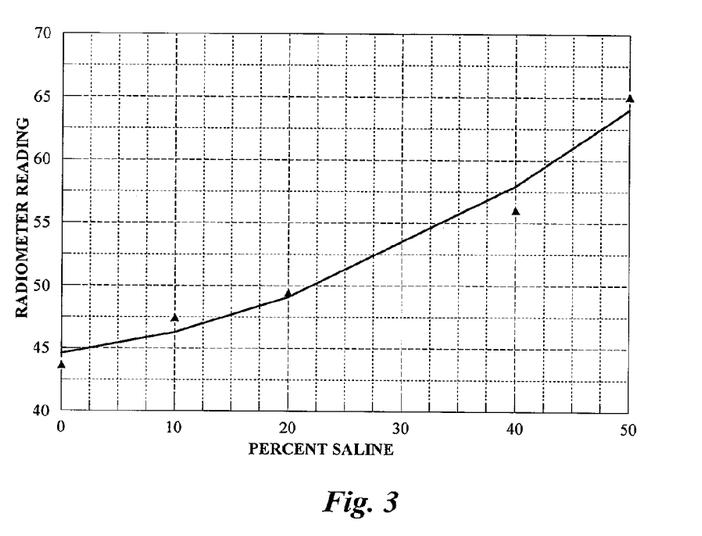
FIG. 3 shows the amount of reflection of injected thermal noise from saline/olive oil emulsions.
Figure 4:
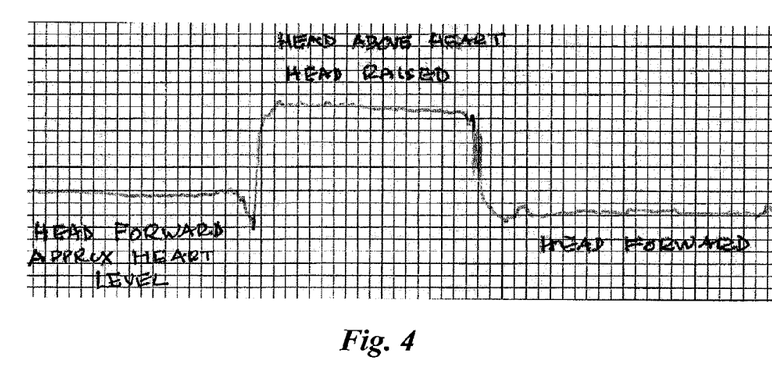
FIG. 4 shows analog output of reflected thermal noise when a thermal noise imaging device is placed against a subject's temple, and the subject's head is moved so as to increase cerebral blood.

FIG. 3 illustrates the large changes in radiometer receiver readings when the radiometer was used to measure the noise power reflected from a mixture of saline (electromagnetic properties similar to that of blood) and olive oil (electromagnetic properties similar to bloodless human fat) that were stabilized by adding a constant amount of flour to each mixture (as described in Lazebnik, cited above).

Example 2

Reflections Indicative of Brain Perfusion

Changes in the perfusion of the brain were be observed by measuring reflected noise power by antennas pressed against the temples of individuals when standing erect or holding their head forward, below the levels of their hearts. The data is illustrated in FIG. 3.

Example 3

Transmission Through Breast Tumor Phantoms

Figure 5:
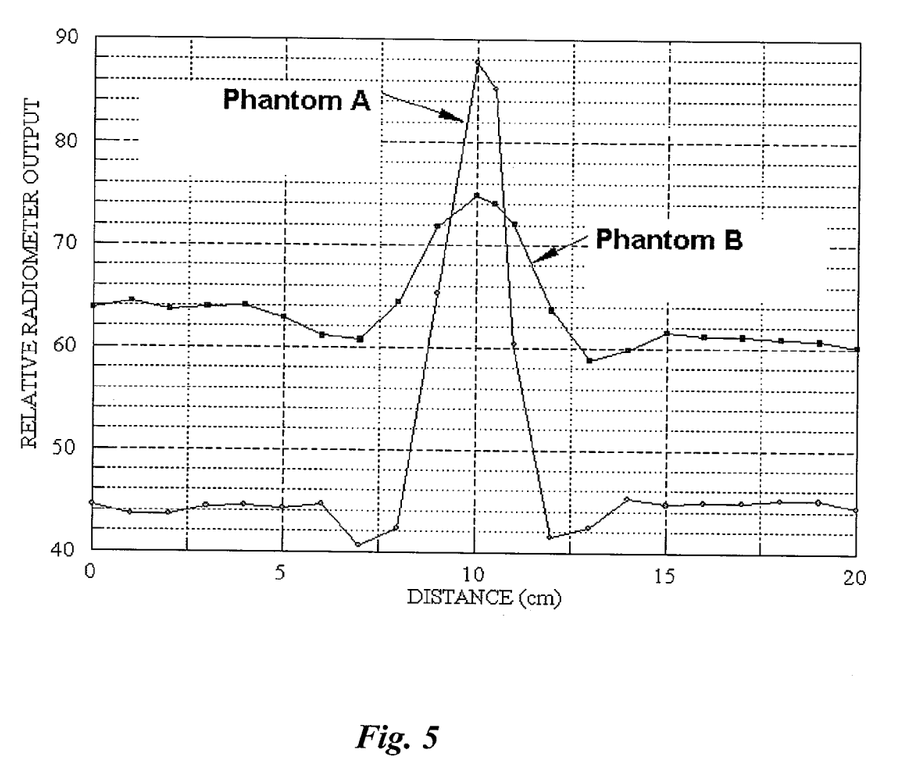
FIG. 5 shows transmission of thermal noise through phantoms with two different simulated tumors.

FIG. 5 shows the results of transmission noise measurements in fat phantoms (no blood) and a small, simulated breast tumor (phantom containing blood). Since blood has a much higher loss factor than the fat, more noise power is absorbed and the transmitted noise power is reduced. Phantom A is for a 6 mm diameter, 8 mm length simulated tumor located a mid-thickness in a 109 mm×215 mm×50 mm thick layer of fat. Phantom B is as before, but with a 40 mm thick layer of fat placed on top.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While the foregoing is directed to embodiments of the present invention, other and further embodiments of the invention may be devised without departing from the basic scope thereof, and the scope thereof is determined by the claims that follow. Any claim below that is written as dependent on an independent claim can also be written as dependent on any of the claims under such independent claim, except where logic forecloses such a dependency.

What is claimed is:

1. A thermal noise imaging device comprising:
   a source of thermal noise device configured to provide thermal noise to an amplifier;
   the amplifier for amplifying the thermal noise from the thermal noise device;
   one or more antennas adapted to transmit the amplified thermal noise to a perfused body and receive resulting perfused body noise, which is the amplified thermal noise after reflection from or transmission through the perfused body;
   a reference circuit adapted to receive the amplified thermal noise and produce a reference signal;
   a perfused body docking interface adapted to interface with one or more surfaces of the perfused body and (i) support a reflection set of one or more of the antennas in close proximity with a surface of the perfused body or (ii) support separate transmission set(s) of one or more of the antennas on opposing surfaces of the perfused body; and
   an analytical module for receiving the resulting perfused body noise and the reference signal and determining one or more of a reflected power from the reflection set and a transmitted power from the transmission sets, to provide thermal noise imaging of the perfused body.

2. The thermal noise imaging device of claim 1, further comprising a positional emitting/receiving imaging or energy emitting device in register with the antennas.

3. The thermal noise imaging device of claim 2, wherein the positional emitting/receiving imaging or energy emitting device comprises:
   an x-ray source; and
   an x-ray detector.

4. The thermal noise imaging device of claim 1, wherein the device comprises opposing transmission sets of antennas, each set of which can be used as a reflection set.

5. The thermal noise imaging device of claim 1, wherein one or more of the antennas is adapted to be used to receive native thermal noise from the perfused body, and the analytical module is operable to determine a perfused body temperature from such native thermal noise.

6. The thermal noise imaging device of claim 1, wherein the perfused body docking interface comprises a compressor for compressing the perfused body comprising two opposing plates, wherein the device comprises opposing transmission sets of antennas positioned respectively on the opposing plates.

7. The thermal noise imaging device of claim 1, wherein the perfused body docking interface comprises a neonatal support and a thoracic plate, wherein the device comprises opposing transmission sets of antennas positioned respectively on the neonatal support and the thoracic plate.

8. The thermal noise imaging device of claim 1, wherein the reflection set or the transmission set comprises said antennas in a number and with a spacing allowing directional transmission and reception as a phased array, and wherein the device comprises a controller that variably controls the timing of transmission or reception at the antennas to provide a range of phased array directionalities.

9. The thermal noise imaging device of claim 1, wherein the device comprises a controller that operates the reflection set or the transmission sets to transmit thermal noise into the perfused body to heat the perfused body or a portion thereof.

10. The thermal noise imaging device of claim 9, wherein the reflection set or the transmission set comprises said antennas in a number and with a spacing allowing directional transmission as a phased array, and wherein the device comprises a controller that variably controls the timing of transmission at the antennas to provide a range of phased array directionalities.

11. The thermal noise imaging device of claim 9, wherein one or more of the antennas can be used to receive native thermal noise from the perfused body, and the analytical module is operable to determine a perfused body temperature from such native thermal noise.

12. A thermal noise imaging method comprising:
 transmitting to a perfused body amplified thermal noise from a device configured to provide thermal noise for use in reflection mode or transmission mode imaging;
 receiving resulting perfused body noise, which is the amplified thermal noise after reflection from or transmission through the perfused body;
 producing a reference signal from the amplified thermal noise;
  from the resulting perfused body noise and the reference signal determining one or more of a reflected power and a transmitted power; and
 utilizing the reflected or transmitted power to provide thermal noise imaging of the perfused body.

13. The thermal noise imaging method of claim 12, further comprising operating a positional emitting/receiving device in register with antennas.

14. The thermal noise imaging method of claim 12, wherein the method comprises determining transmitted power.

15. The thermal noise imaging method of claim 12, wherein the method comprises determining reflected power.

16. The thermal noise imaging method of claim 12, further comprising receiving native thermal noise from the perfused body and determining a perfused body temperature from such native thermal noise.

17. The thermal noise imaging method of claim 12, further comprising compressing the perfused body and determining power transmitted through the compressed perfused body.

18. The thermal noise imaging method of claim 12, further comprising determining power transmitted through the thorax of a neonate.

19. The thermal noise imaging method of claim 12, further comprising utilizing phased arrays of antennas to transmit amplified thermal noise or receive the perfused body noise with a range of directionalities.

20. The thermal noise imaging method of claim 12, further comprising transmitting thermal noise into the perfused body to heat the perfused body or a portion thereof.

21. The thermal noise imaging method of claim 20, further comprising utilizing phased arrays of antennas to transmit the thermal noise for heating with a range of directionalities.

22. The thermal noise imaging method of claim 20, further comprising receiving native thermal noise from the perfused body, and determining a perfused body temperature from such native thermal noise.

\* \* \* \* \*